United States Patent
Miles et al.

(10) Patent No.: US 11,479,520 B2
(45) Date of Patent: Oct. 25, 2022

(54) SYSTEM AND PROCESS FOR CONVERTING LIGHT ALKANE TO AROMATICS

(71) Applicants: China Energy Investment Corporation Limited, Beijing (CN); National Institute of Clean-and-Low-Carbon Energy, Beijing (CN)

(72) Inventors: Joshua Miles, San Francisco, CA (US); Hui Wang, Fremont, CA (US); Junjun Shan, San Jose, CA (US); Jihong Cheng, Santa Clara, CA (US); Anthony Ku, Fremont, CA (US); Lisa Nguyen, Santa Clara, CA (US)

(73) Assignees: China Energy Investment Corporation Limited, Beijing (CN); National Institute of Clean-and-Low-Carbon Energy, Beijing (CN)

( * ) Notice: Subject to any disclaimer, the term of this patent is extended or adjusted under 35 U.S.C. 154(b) by 2 days.

(21) Appl. No.: 17/228,837

(22) Filed: Apr. 13, 2021

(65) Prior Publication Data

US 2021/0323895 A1 Oct. 21, 2021

(30) Foreign Application Priority Data

Apr. 21, 2020 (CN) .......................... 202010318095.7

(51) Int. Cl.
*C07C 2/76* (2006.01)
*C07C 2/42* (2006.01)
*C07C 5/327* (2006.01)

(52) U.S. Cl.
CPC .................. *C07C 2/76* (2013.01); *C07C 2/42* (2013.01); *C07C 5/327* (2013.01)

(58) Field of Classification Search
CPC .. C07C 2/76; C07C 2/42; C07C 5/327; C07C 2529/40
See application file for complete search history.

(56) References Cited

U.S. PATENT DOCUMENTS

| | | |
|---|---|---|
| 4,120,910 A | 10/1978 | Chu |
| 4,642,403 A | 2/1987 | Hyde et al. |

(Continued)

FOREIGN PATENT DOCUMENTS

| | | |
|---|---|---|
| CN | 101910094 A | 12/2010 |
| CN | 102159522 A | 8/2011 |

(Continued)

*Primary Examiner* — Ali Z Fadhel
(74) *Attorney, Agent, or Firm* — Calfee Halter & Griswold LLP

(57) ABSTRACT

A system and a method are provided for producing aromatics. Such a system includes a cracker unit configured to convert a light alkane into an olefin-containing hydrocarbon comprising at least one alkene, and an aromatization unit. The light alkane is selected from the group consisting of methane, ethane, propane, butane, and a combination thereof. The cracker unit is configured to at least partially feed the olefin-containing hydrocarbon into the aromatization unit. Such an olefin-containing hydrocarbon comprises at least 40 wt. % of the at least one alkene. The aromatization unit is used to convert the olefin-containing hydrocarbon therein into a product stream, which includes an aromatic hydrocarbon selected from the group consisting of benzene, toluene, xylenes, and a combination thereof.

21 Claims, 9 Drawing Sheets

(56) References Cited

U.S. PATENT DOCUMENTS

| | | |
|---|---|---|
| 9,321,703 B2 | 4/2016 | Nyce et al. |
| 2014/0100398 A1* | 4/2014 | Jin .......................... C10G 55/06 585/254 |
| 2017/0144947 A1* | 5/2017 | Keusenkothen ..... B01J 29/7661 |
| 2021/0016261 A1 | 1/2021 | Wang et al. |

FOREIGN PATENT DOCUMENTS

| | | |
|---|---|---|
| CN | 112830858 A | 5/2021 |
| EP | 0785178 B1 | 3/1999 |
| KR | 20150016440 A | 2/2015 |

* cited by examiner

SYSTEM AND PROCESS FOR CONVERTING LIGHT ALKANE TO AROMATICS

PRIORITY CLAIM AND CROSS-REFERENCE

This application claims the priority of Chinese Patent Application No. 202010318095.7, filed Apr. 21, 2020, which application is expressly incorporated by reference herein in its entirety.

FIELD OF THE INVENTION

The disclosure relates to petrochemical processing generally. More particularly, the disclosed subject matter relates to a method for making aromatic hydrocarbons from light alkanes and/or alkenes.

BACKGROUND

The conversion of light hydrocarbons to aromatics is important because it provides a route for producing high value aromatic hydrocarbons, such as benzene, toluene and xylenes (BTX), from less expensive feedstock, such as methane and olefins. Providing aromatics from relatively inexpensive feedstock is an economically attractive way to produce raw materials. Benzene, toluene, and xylene are very important petrochemical raw materials for polymer and other petrochemical syntheses. For example, BTX can be used as precursors for styrene monomer and other derivatives for synthesis.

The process by which light alkanes and alkenes are converted into aromatic products is a catalytic aromatization reaction, which is a complex reaction that can include the steps of dehydrogenation, oligomerization, and aromatization.

EP 0785178 B1 describes a method for converting light hydrocarbon feedstock comprising at least one member selected from the group consisting of olefins and paraffins to a fixed-bed, adiabatic reactor containing a fixed catalyst bed made of a zeolite catalyst. The light hydrocarbon feedstock contact with the catalyst to produce an aromatic hydrocarbon product stream. This process requires a stream including primarily C5 olefins in order for the process to generate on-demand aromatic hydrocarbons.

U.S. Pat. No. 9,321,703 describes a process for converting methane to ethylene, and then converting ethylene to higher hydrocarbons by use of an ethylene-to-liquids (ETL) reactor. This reactor uses an oligomerization process that gives a mixture of various products with the intention of creating a C4-C5 product stream to be used as a blend stock for fuels.

SUMMARY

The present disclosure provides a system and a method for producing aromatics. In accordance with some embodiments, such a system includes a cracker unit configured to convert a light alkane into an olefin-containing hydrocarbon comprising at least one alkene, and an aromatization unit. In some embodiments, the light alkane is selected from the group consisting of methane, ethane, propane, butane, and a combination thereof. The cracker unit is configured to at least partially feed the olefin-containing hydrocarbon into the aromatization unit. Such an olefin-containing hydrocarbon comprises at least 40 wt. % of the at least one alkene.

The aromatization unit is configured to convert the olefin-containing hydrocarbon therein into a product stream, which includes an aromatic hydrocarbon selected from the group consisting of benzene, toluene, xylenes, and a combination thereof. A resulting product may be benzene, toluene, xylenes, or a combination thereof. In some embodiments, the resulting product includes benzene, toluene, and xylenes (BTX).

In some embodiments, the cracker unit includes a steam cracker, or any other suitable cracker. The feedstock can be any light alkane, or a mixture of light alkane and olefin. In some embodiments, the light alkane is ethane, and the at least one alkene comprises at least 40 wt. % of ethylene, and optionally propylene.

In some embodiments, the cracker unit comprises a cracker reactor and optionally a cracker separator. The aromatization unit comprises an aromatization reactor and optionally an aromatization separator. The cracker reactor is configured to feed a first stream of the olefin-containing hydrocarbon into the aromatization reactor, and optionally feed a second stream of the olefin-containing hydrocarbon into the cracker separator. The first and the second stream can be at any ratio. For example, the first stream can be 10-100% of the olefin-containing hydrocarbon stream from the cracker unit, the second stream can be 0-90% of the olefin-containing hydrocarbon stream from the cracker unit. The cracker separator is configured to separate the second stream of the olefin-containing hydrocarbon to provide an ethylene stream and a propylene stream.

The aromatization reactor is configured to direct the product stream comprising an aromatic hydrocarbon into the aromatization separator. The aromatization separator is configured to separate the product stream to provide a first product comprising benzene, toluene, xylenes, or a combination thereof. The aromatization separator is configured to further provide a second product comprising C8+ hydrocarbon.

In addition, the aromatization separator may be configured to separate a hydrocarbon-containing residue gas from the product stream and direct the alkane-containing residue gas into the cracker separator. The cracker separator is configured to separate an alkane-containing gas therein and recycle the alkane-containing gas back to the cracker reactor.

In some embodiments, in addition to the cracker unit and the aromatization unit, the system may further comprise a compress unit configured to condense the product stream comprising an aromatic hydrocarbon from the aromatization unit to provide a liquid product stream and a gas product stream. A liquid separator is coupled with the compression unit configured to separate the liquid product stream to provide an aromatic hydrocarbon selected from the group consisting of benzene, toluene, xylenes, and a combination thereof.

In another aspect, the present disclosure provides a method for producing aromatics. Such a method comprises steps of providing a light alkane into a cracker unit, converting the light alkane into an olefin-containing hydrocarbon comprising at least one alkene inside the cracker unit, and feeding a first stream of the olefin-containing hydrocarbon from the cracker unit into an aromatization reactor in an aromatization unit fluidly coupled with the cracker unit. In some embodiments, the light alkane comprises an alkane selected from the group consisting of methane, ethane, propane, butane, and a combination thereof. The first stream of the olefin-containing hydrocarbon stream comprises at least 40 wt. % of the at least one alkene (e.g., ethane).

The first stream of the olefin-containing hydrocarbon includes a portion or all of the olefin-containing hydrocarbon inside the cracker unit. In some embodiments, the light alkane comprises or is ethane, and the at least one alkene comprises 40 wt. % of ethylene, and optionally propylene.

Such a method further comprises converting the olefin-containing hydrocarbon inside an aromatization reactor in an aromatization unit into a product stream. A catalyst as described below can be used. The product stream comprises an aromatic hydrocarbon selected from the group consisting of benzene, toluene, xylenes, and a combination thereof. The method may further comprise separating the product stream to a first product comprising benzene, toluene, xylenes, or a combination thereof, and optionally a second product comprising C8+ hydrocarbons. In some embodiments, wherein the first product comprises benzene, toluene, and xylenes (BTX).

In some embodiments, the first stream of the olefin-containing hydrocarbon is converted into the aromatic hydrocarbon with a selectivity of higher than 40%, in a range of from 40-100%, for example, in a range of from 40% to 90%, from 50% to 90%, and from 50% to 80%.

In some embodiments, the method further comprises: feeding a second stream of the olefin-containing hydrocarbon into a cracker separator in the cracker unit, and separating the second stream of the olefin-containing hydrocarbon inside the cracker separator to provide an ethylene stream and a propylene stream.

In some embodiments, the method further comprises separating a hydrocarbon-containing residue gas from the product stream, directing the alkane-containing residue gas into the cracker separator, separating an alkane-containing gas in the cracker separator, and recycling the alkane-containing gas back to the cracker reactor.

In some embodiments, an integrated system includes a cracker unit, an aromatization unit, and a compress unit connected in series. The method further comprises condensing the product stream comprising an aromatic hydrocarbon using a compression unit fluidly coupled with the aromatization unit to provide a liquid product stream and a gas product stream, and separating the liquid product stream in a liquid separator fluidly coupled with the condenser to provide an aromatic hydrocarbon selected from the group consisting of benzene, toluene, xylenes, and a combination thereof.

In the method provided in the present disclosure, the steps are performed continuously and/or concurrently in an integrated system. Sometimes, the method can be performed in a batch process.

With the system including the catalyst described herein, the method provided in the present disclosure can be used to aromatize alkanes and/or alkenes with high selectivity in providing an aromatic hydrocarbon such as one or more BTX products. The system and the method can be also used to tailor or adjust the ratio of the products between BTX products and an alkene including ethylene and/or propylene. Such adjustment is highly flexible. With light alkane or alkene as feedstock, the method is also cost-effective.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

Figure 1:
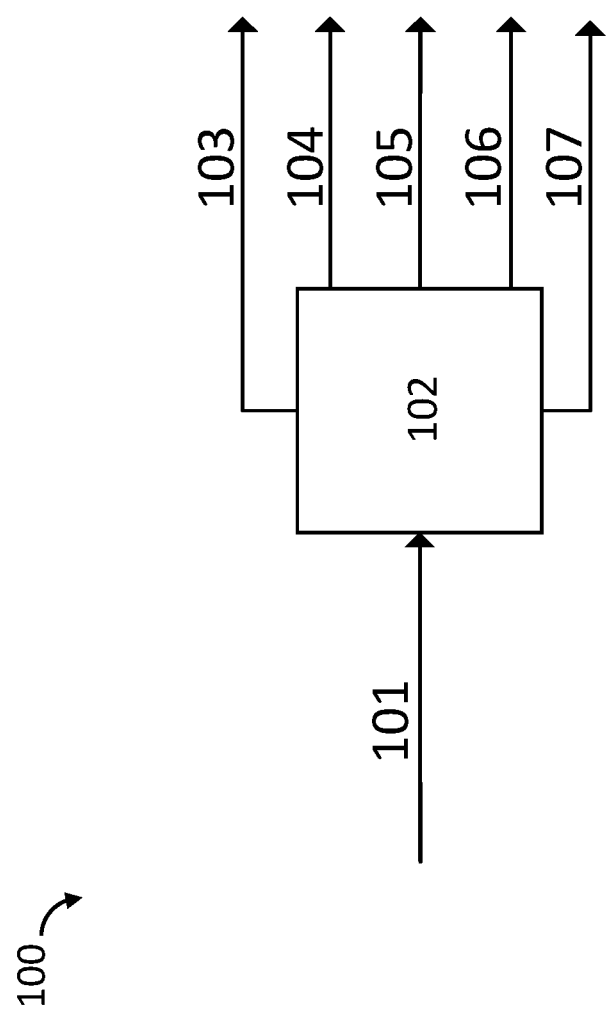
FIG. 1 illustrates an exemplary ethane cracker unit or sub-system comprising an ethane cracker unit in some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" refer to a relationship wherein structures are secured or attached to one another either directly or indirectly through intervening structures, as well as both movable or rigid attachments or relationships, unless expressly described otherwise.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. Thus, for example, a reference to "a reactor" or "a hydrocarbon" is a reference to one or more of such structures and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to (but not always) refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

With current trend in oil industry shifts from fuel to chemical production, aromatic compounds are more attractive products compared to fuel.

Light alkanes such as ethane are mainly used as feed stock to produce olefins in some embodiments. One of the key processes is steam cracking. Steam cracking is a petrochemical process, in which saturated hydrocarbons such as naphtha are broken down into smaller, often unsaturated, hydrocarbons. It is the principal industrial method for producing the lighter alkenes such as ethylene and propylene. Aromatics can be also recovered from steam cracking, which accounts for $1/3$ of total aromatics production worldwide. When ethane is used as the only feedstock in some embodiments, aromatics yield drops to near zero, which breaks the balance within chemical industry. A process that integrates ethane cracker and aromatization provided in the present disclosure can solve the imbalance.

Because of the relatively inexpensive price of ethane and ethylene and the readily available feedstock, it is desirable to have aromatization of alkanes or alkenes to produce light aromatics (e.g., BTX). For example, compared to C5 olefins, lower alkanes such as ethane can be much more cost-effective feedstock for aromatics production.

The present disclosure provides a system and a process for producing aromatics such as benzene, toluene, and xylenes (BTX) comprising aromatization of alkanes and/or alkenes. The present disclosure also provides a process to convert a cracker product stream into BTX, and a system comprising an aromatization reactor and a BTX recovery unit. The system and the method provided in the present disclosure recognize the need for the efficient and commercially viable aromatic production systems and methods for converting alkenes, including ethylene and propylene, through the aromatization of the olefinic feed gas stream comprising at least 40 wt. % such as at least 50 wt. % olefin such as ethylene.

In FIGS. 1-6, like items are indicated by like reference numerals, and for brevity, descriptions of the structure, provided above with reference to the preceding figures, are not repeated. The method described in FIGS. 7A-7C is described with reference to the exemplary structure described in FIGS. 1-6, particularly FIGS. 3-6.

Unless expressly indicated otherwise, each block in the figures represents a structural unit or a group of units, each arrow represents a stream of reactant or product, all the units are fluidly coupled together as shown. The term "fluidly coupled" or "fluidly connected" is understood to mean that the units are connected with pipes, valves and related structures so that gas or liquid stream can flow from one unit to another unit. The system described herein can be operated continuously with the steps performed concurrently. In some embodiments, the system may be operated in a batch process. In the cracking and aromatization processes, suitable catalyst, temperature, pressure, and other conditions are also used.

Unless expressly indicated otherwise, the percentages (%) described herein are by weight. The method and the system provided in the present disclosure may also be applicable if the percentages are by volume or by moles.

Unless expressly indicated otherwise, the term "light alkane" described herein is understood to encompass one or more alkanes having one to five carbons. For example, such a light alkane is selected from the group consisting of methane, ethane, propane, butane, and a combination thereof. In some embodiments, ethane is used as the feedstock of light alkane.

Unless expressly indicated otherwise, the term "an aromatic hydrocarbon" described herein is understood to encompass one or more aromatic hydrocarbons. For example, such an aromatic hydrocarbon is selected from the group consisting of benzene, toluene, xylenes, and a combination thereof. Xylenes include different xylenes having different locations of substitution. A resulting product may be benzene, toluene, xylenes, or a combination thereof. In some embodiments, the resulting product includes benzene, toluene, and xylenes (BTX).

In the present disclosure, the olefinic product stream from the cracker facility is integrated in order to create on-demand aromatic hydrocarbons using an aromatization reactor and a BTX recovery or separation unit. In some embodiments, this novel process incorporates an ethane cracker unit as the olefinic source for an aromatization reactor for the production of on-demand aromatics.

The system and the method provided in the present disclosure provide several benefits, including but not limited to:

1. Allowing for a process to directly produce aromatics on demand;
2. Increasing the product slate of an ethane cracker unit;
3. Having a flexible process that can produce olefins and aromatics with tunable ratio depending on the market demand; and
4. Revamping an ethane cracker by adding aromatization unit and associated liquid product separation.

Referring to FIG. 1, an exemplary cracker sub-system 100 includes an ethane cracker unit 102.

Stream 101 is the primary ethane feed to the ethane cracker unit 102. The primary product streams from the ethane cracker unit 102 include the ethylene product stream 103 and the propylene product stream 104. Additionally, the product streams include a pyrolysis gas stream 105, a light distillate stream 106, and a crude C4 or C4+ product stream 107, as secondary product streams. In some embodiments, the gas stream 105 or the light distillate stream may include hydrogen or methane. These five product streams are the main outputs from the ethane cracker unit 102.

Figure 2:
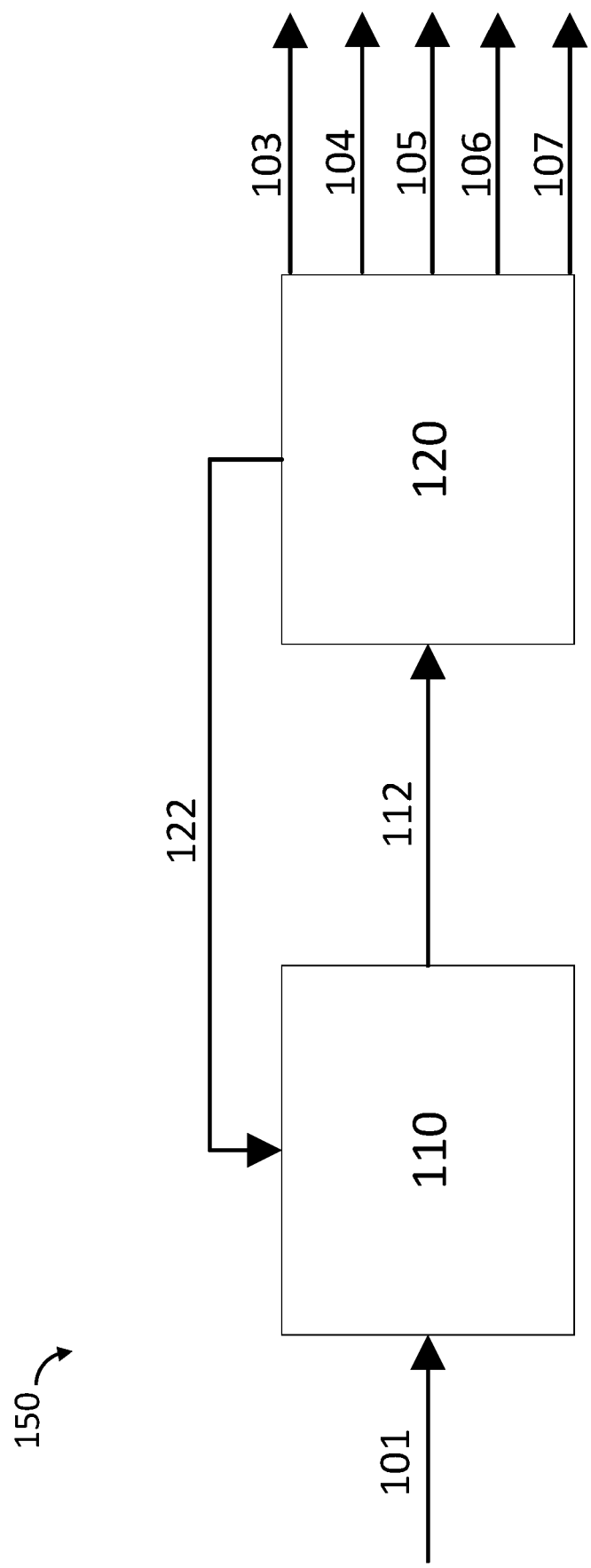
FIG. 2 is a block flow diagram (BFD) illustrating an exemplary ethane cracker unit or sub-system including an ethane cracker reactor and an ethane cracker separator in accordance with some embodiments.

Referring to FIG. 2, an exemplary ethane cracker unit or sub-system 150 includes an ethane cracker reactor 110 and an ethane cracker separator 120 in accordance with some embodiments. The exemplary ethane cracker sub-system 150 is an example of the exemplary ethane cracker sub-system 100 in some embodiments.

In FIG. 2, an alkane stream 101, which is the feed stream to the entire process, comprises or consists of ethane gas. The alkane stream may optionally include other light alkanes such as propane in some embodiments.

Alkane stream 101 comprising ethane gas is fed to the ethane crack reactor 110. Inside the ethane cracker reactor 110, alkane stream 101 is chemically converted into an alkene-containing stream 112, and the ethane is converted primarily into ethylene and propylene. All the effluent of the ethane cracker reactor 110, i.e., the alkene-containing stream 112 is fed to the ethane cracker separator 120. Inside the ethane cracker separator 120, an alkene-containing stream 112 is separated into at least five product streams. These streams include the ethylene product stream 103, and the propylene product stream 104 as the primary products as described in FIG. 1. Additionally, the secondary products may include a gas stream 105 including hydrogen, a light distillate stream 106, which may include methane, and a, a crude C4 or C4+ product stream 107, as secondary product streams. The unreacted gas 122 including ethane and propane is recycled back to the feed of the ethane cracker reactor 110.

Figure 3:
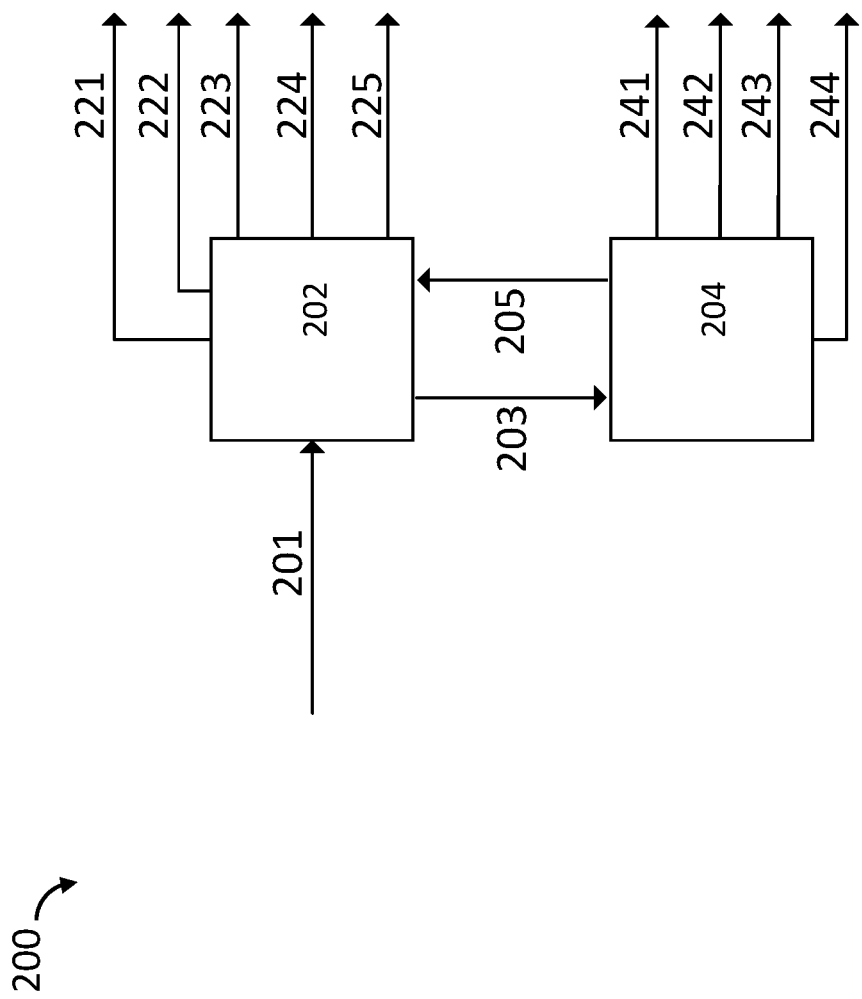
FIG. 3 is a block flow diagram illustrating a first exemplary system including an ethane cracker unit and an aromatics production unit in accordance with some embodiments.

In accordance with some embodiments, a system includes a cracker unit (e.g., cracker unit 202 in FIG. 3) configured to convert a light alkane into an olefin-containing hydrocarbon comprising at least one alkene, and an aromatization unit (e.g., unit 204 in FIG. 3). In some embodiments, the light alkane is selected from the group consisting of methane, ethane, propane, butane, and a combination thereof. The cracker unit is configured to at least partially feed the olefin-containing hydrocarbon into the aromatization unit. Such an olefin-containing hydrocarbon comprises at least 50 wt. % of the at least one alkene. The aromatization unit is configured to convert the olefin-containing hydrocarbon therein into a product stream, which includes an aromatic hydrocarbon selected from the group consisting of benzene, toluene, xylenes, and a combination thereof. A resulting product may be benzene, toluene, xylenes, or a combination thereof. In some embodiments, the resulting product includes benzene, toluene, and xylenes (BTX).

Referring to FIG. 3, a first exemplary system 200 includes a cracker unit 202 such as an ethane cracker unit and an aromatization unit or aromatics product unit 204 in accordance with some embodiments.

In some embodiments, the cracker unit 202 is a steam cracker, or any other suitable cracker. The feedstock (i.e. alkane stream) can be any light alkane, or a mixture of light alkane and olefin. Alkane stream 201 is the primary ethane feed to the cracker unit 202. Alkane stream 201 has the same composition as alkane stream 101 as described above. The alkane stream 201 comprises or consists of ethane gas. The alkane stream may optionally include other light alkanes such as propane in some embodiments.

The primary product streams from the cracker unit 202 are the ethylene product stream 221 and the propylene product stream 222. Additionally, the product streams may include a crude C4 or C4+ product stream 223, a light distillate stream 224 (e.g., methane), and a pyrolysis gas stream 225 (e.g., hydrogen) as secondary product streams. The streams 223, 224 and 225 may have the same compositions as the stream 105, 106, and 107, respectively, as described above.

Stream 203, referred as the first stream of the olefin-containing hydrocarbon stream from the cracker unit 202, is an intermediate stream comprising ethylene, propylene, or a combination thereof. In some embodiments, stream 203 comprises at least 40% such as at least 50% ethylene, and may include another ingredient including, but not limited to, ethane, propane, propylene, butane, butadiene, acetylene, or a combination thereof. This stream 203 is fed to the aromatization unit 204, which may include an aromatization reactor and a separator. Stream 205 is a recycled stream from unit 204 back to the cracker unit 202. This stream 205 may comprise ethane, propane, methane and hydrogen, and may include other ingredients including, but not limited to, ethylene, propylene, butane, butadiene and acetylene, or a combination thereof.

The primary product streams of the aromatization unit 204 include the BTX product stream 241, the C8+ stream or heavy fuel oil stream 242. In addition, secondary product streams from unit 204 may include a fuel gas stream 243 and a hydrogen stream 244. Unless expressly indicated otherwise, the ingredients in a BTX product stream such as stream 241 may include at least one of benzene, toluene, xylenes, or any combination thereof. In some embodiments, the BTX products include a mixture of such as benzene, toluene and xylenes.

The first exemplary system 200 in FIG. 3 shows a general concept of a system and a method provided in the present disclosure. The various product streams of an integrated system provided in the present disclosure, when added to the product streams of a cracker unit 202, help to diversify the products of the cracker unit 202. The cracker unit 202 with the added BTX product streams can better meet market demands concerning benzene, toluene and xylene.

In the systems provided in the present disclosure including the first exemplary system 200, an ethylene rich stream (i.e. stream 203) from a cracker unit such as an ethane cracker unit 202 is converted into aromatics including benzene, toluene, xylenes, or a combination thereof. The conversion of ethylene is expected to be at least 50%, for example, 50%, 60%, or 70%, with a selectivity to BTX of at least 40%, for example, 40%, 50%, or 60%, in accordance with some embodiments. This allows for on demand production of aromatic compounds to help diversify the product slate of a cracker facility.

In some embodiments, the cracker unit comprises a cracker reactor and optionally a cracker separator. The aromatization unit comprises an aromatization reactor and optionally an aromatization separator. The cracker reactor is configured to feed a first stream of the olefin-containing hydrocarbon into the aromatization reactor, and optionally feed a second stream of the olefin-containing hydrocarbon into the cracker separator. The first and the second stream can be any ratio. For example, the first stream can be 10-100% of the olefin-containing hydrocarbon stream from the cracker unit, the second stream can be 0-90% of the olefin-containing hydrocarbon stream from the cracker unit. The cracker separator is configured to separate the second stream of the olefin-containing hydrocarbon to provide an ethylene stream and a propylene stream. The aromatization reactor is configured to direct the product stream comprising an aromatic hydrocarbon into the aromatization separator. The aromatization separator is configured to separate the product stream to provide a first product comprising benzene, toluene, xylenes, or a combination thereof. The aromatization separator is configured to further provide a second product comprising C8+ hydrocarbon.

Figure 4:
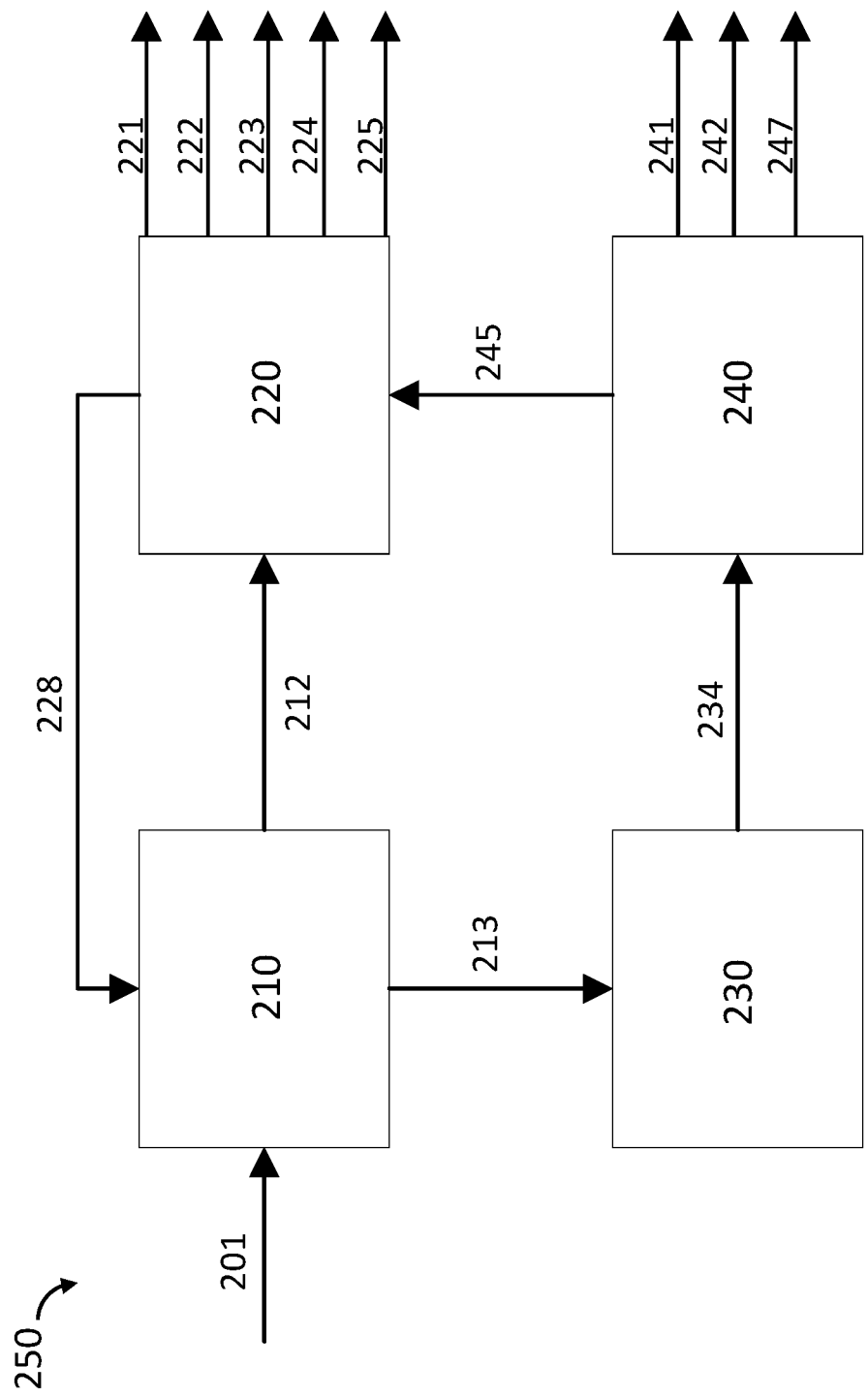
FIG. 4 illustrates a second exemplary system including an ethane cracker unit and an aromatics production unit in accordance with some embodiments.

Referring to FIG. 4, a second exemplary system 250 is illustrated. The second exemplary system 250 includes a cracker reactor 210 such as an ethane cracker reactor, a cracker separator 220, an aromatization reactor 230, and an aromatization separator 240. The second exemplary system 250 is a detailed illustration of the first exemplary system 200 in accordance with some embodiments. The cracker reactor 210 and the cracker separator 220 may be an example of the cracker unit 202 in FIG. 3. The aromatization reactor 230 and the aromatization separator 240 may be an example of the aromatics production unit 204.

In FIG. 4, stream 201 is the feed stream of raw material to the entire process in the second exemplary system 250. In some embodiments, the stream 201 comprises or consists of ethane gas. The ethane gas is fed to the cracker reactor 210. Inside the cracker reactor 210 such as an ethane cracker reactor, ethane is converted primarily into ethylene and propylene. The effluent gas from the cracker reactor 210 include streams 212 and 213. Stream 213, referred as the first stream, is fed to the aromatization reactor 230. Optionally, stream 212, referred as the second stream, is fed to the ethane cracker separator 220 for separation. In some embodiments, stream 213 is the same as stream 203 in FIG. 3.

In the aromatization reactor 230, the ethane cracker effluent in stream 213 is converted into aromatics (i.e. BTX) and heavies (C8+) product. The effluent 234 of the aromatization reactor 230 is fed to the aromatization separator 240 and is separated into different product streams. In some embodiments, the product streams from the aromatization separator 240 include the BTX product stream 241, the heavies product stream 242 comprising C8+ products stream, and stream 247 comprising the C4+ product. These product streams are separated from lower value gases 245. At least the BTX product stream 241 and the heavies product stream 242 are two new products provided compared to the systems in FIGS. 1-2.

In addition, the aromatization separator 240 may be configured to separate a hydrocarbon-containing residue gas (e.g., gases 245) from the product stream and direct the alkane-containing residue gas into the cracker separator 220. The cracker separator 220 is configured to separate an alkane-containing gas (e.g., gas 228) therein and recycle the alkane-containing gas back to the cracker reactor 210.

In some embodiments, additional secondary product streams from the aromatization separator 240 may include a fuel gas stream 243 and a hydrogen stream 244. Similar to the stream 205, the lower value gases 245 may comprise ethane, propane, methane and hydrogen, and may include other ingredients including, but not limited to, ethylene, propylene, butane, butadiene and acetylene, or a combination thereof. The lower value gases 245 can be recycled and fed into the cracker separator 210.

The primary product streams from the cracker separator 220 are the ethylene product stream 221 and the propylene product stream 222. Additionally, the product streams may include a crude C4 or C4+ product stream 223, a light distillate stream 224, and a pyrolysis gas stream 225 as secondary product streams. In some embodiments, the light distillate stream comprises methane. The pyrolysis gas stream may include hydrogen gas. The remainder stream 228 of the gases inside the cracker separator 220 may be fed back to the ethane cracker reactor 210 and mixed with the gases therein. The unreacted ethane and propane in the stream 228 are recycled back to the ethane cracker reactor 210.

Streams 212 and 213 can be adjusted in any suitable ratio. For example, 20% of the effluents from the ethane cracker reactor 210 can be used as the stream 213 fed to the aromatization reactor 230, and 80% of the effluents from the cracker reactor 210 can be the stream 212 fed to the cracker separator 220. For another example, 60% of effluents from the ethane cracker reactor 210 can be used as the stream 213 fed to the aromatization reactor 230, and 40% of the effluents from the ethane cracker reactor 210 can be the stream 212 fed to the ethane cracker separator 220.

Figure 5:
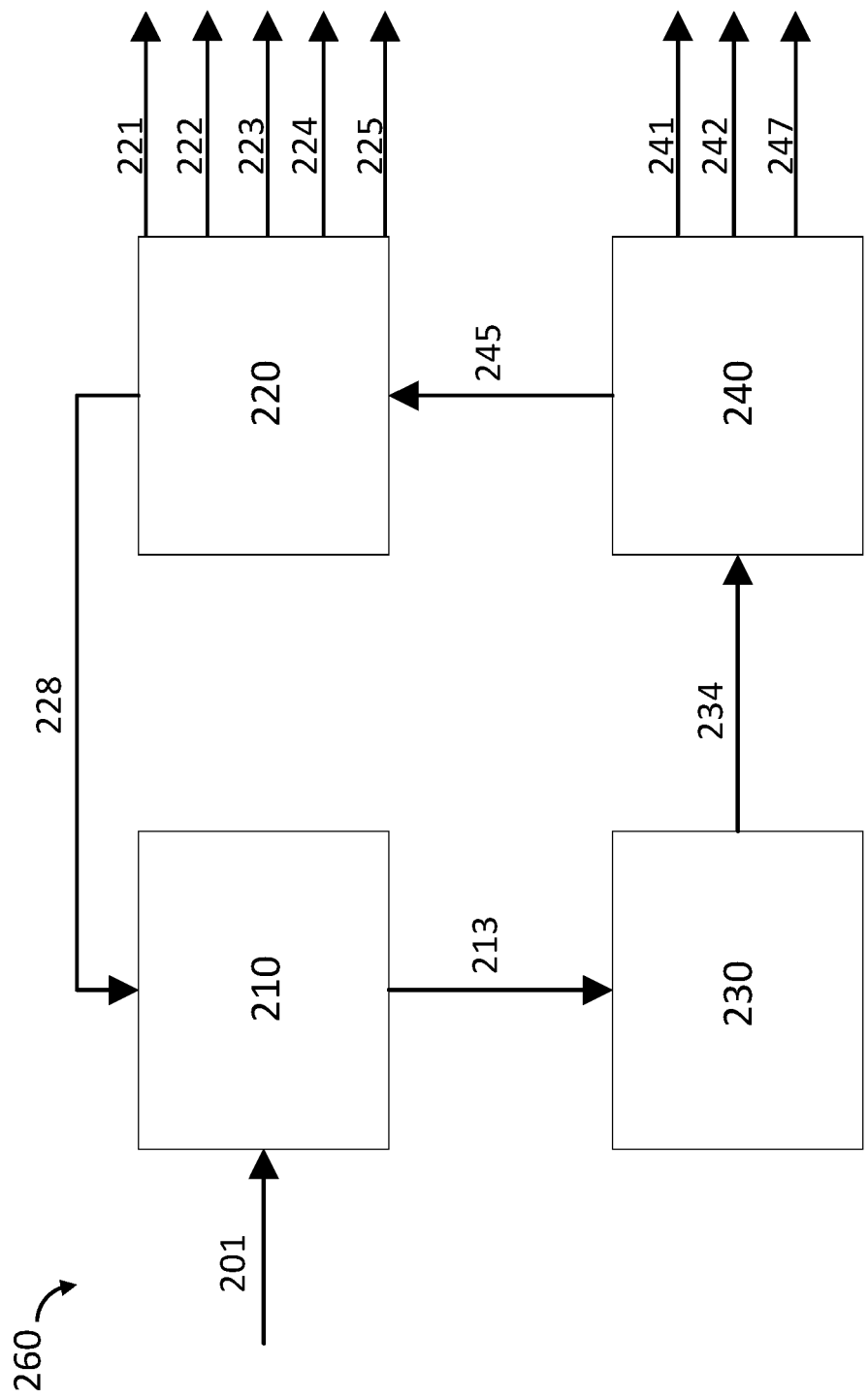
FIG. 5 illustrates a third exemplary system including an ethane cracker unit and an aromatics production unit in accordance with some embodiments.

Referring to FIG. 5, a third exemplary system 260 also includes a cracker reactor 210, a cracker separator 220, an aromatization reactor 230, and an aromatization separator 240. Third exemplary system 260 is the same as the second exemplary system 250 Case 4, except that the third exemplary system is configured to feed 100% of the effluent of the ethane cracker reactor 210 as the stream 213 to the aromatization reactor 230. As described in FIG. 3, the BTX product stream 241 and the heavies product stream 242 are two new products obtained.

In FIG. 5, stream 201 is the feed stream of raw material to the entire process in the second exemplary system 260. In some embodiments, the stream 201 comprises or consists of ethane gas. The ethane gas is fed to the ethane cracker reactor 201. Inside the ethane cracker reactor 210, ethane is converted primarily into ethylene and propylene. The effluent gas from the ethane cracker reactor 210 as stream 213 is fed to the aromatization reactor 230. In the aromatization reactor 230, the ethane cracker effluent in stream 213 is converted into aromatics (i.e. BTX) and heavies (C8+) product. The effluent 234 of the aromatization reactor 230 is fed to the aromatization separator 240 and is separated into different product streams.

In some embodiments, the product streams from the aromatization separator 240 include the BTX product stream 241, the heavies product stream 242 comprising C8+ products stream, and stream 247 comprising the C4+ product. These product streams are separated from lower value gases 245. The lower value gases 205 can be recycled and fed into the ethane cracker separator 220.

The primary product streams from the ethane cracker separator 220 are the ethylene product stream 221 and the propylene product stream 222. Additionally, the product streams may include a crude C4 or C4+ product stream 223, a light distillate stream 224, and a pyrolysis gas stream 225 comprising hydrogen. The remainder stream 228 of the gases inside the ethane cracker separator 220 may be fed back to the ethane cracker reactor 210 and mixed with the gases therein. The unreacted ethane and propane in the stream 228 are recycled back to the ethane cracker reactor 210.

In some embodiments, in addition to the cracker unit and the aromatization unit, the system may further comprise a compress unit configured to condense the product stream comprising an aromatic hydrocarbon from the aromatization unit to provide a liquid product stream and a gas product stream. A liquid separator is coupled with the compression unit configured to separate the liquid product stream to provide an aromatic hydrocarbon selected from the group consisting of benzene, toluene, xylenes, and a combination thereof.

Figure 6:
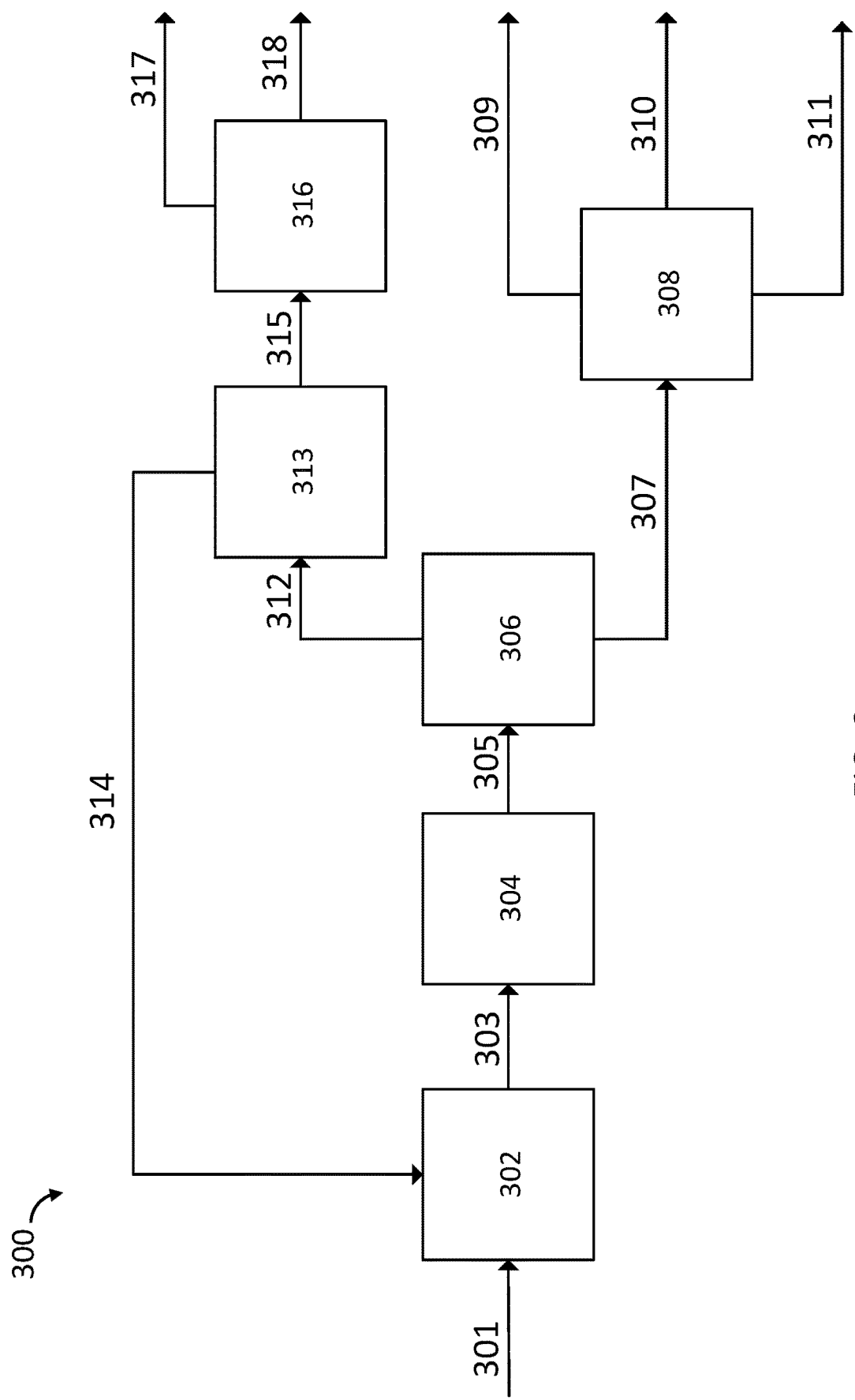
FIG. 6 illustrates a fourth exemplary system including an ethane cracker unit and an aromatics production unit in accordance with some embodiments.
Figure 7A:
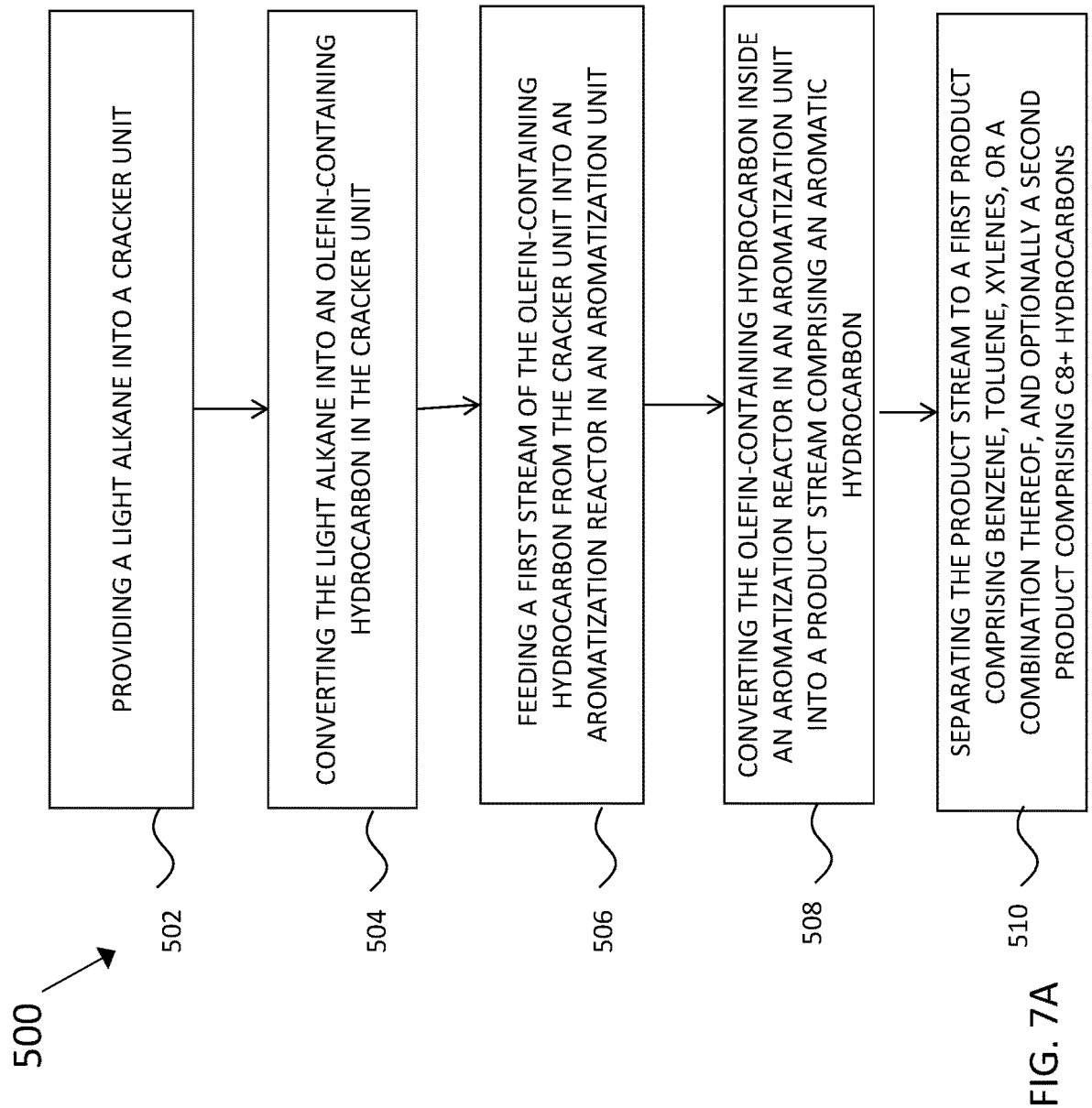
FIG. 7A-7C are flow charts illustrating an exemplary method for making aromatic hydrocarbons from light alkanes and/or alkenes.
Figure 7B:
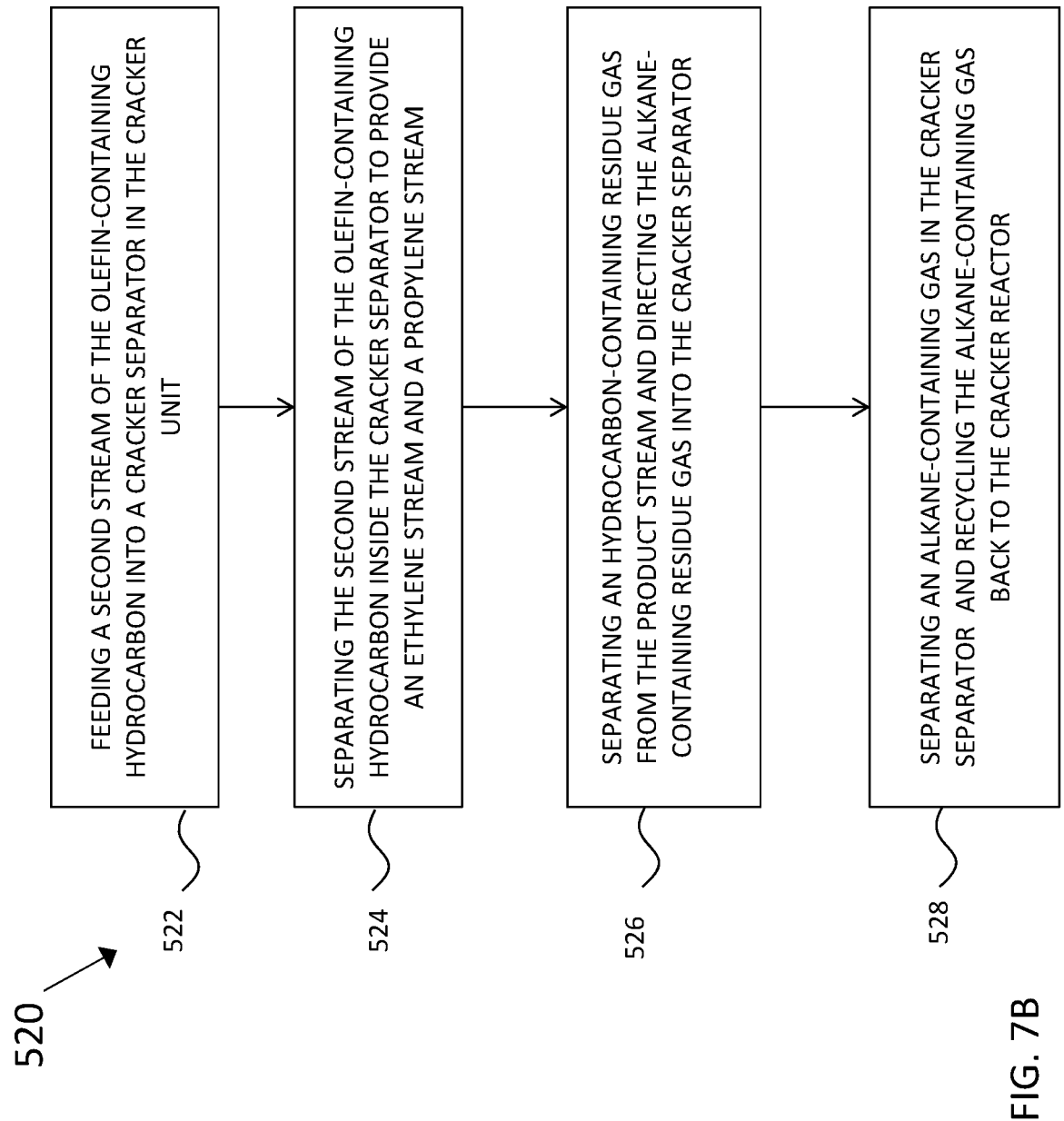
Figure 7C:
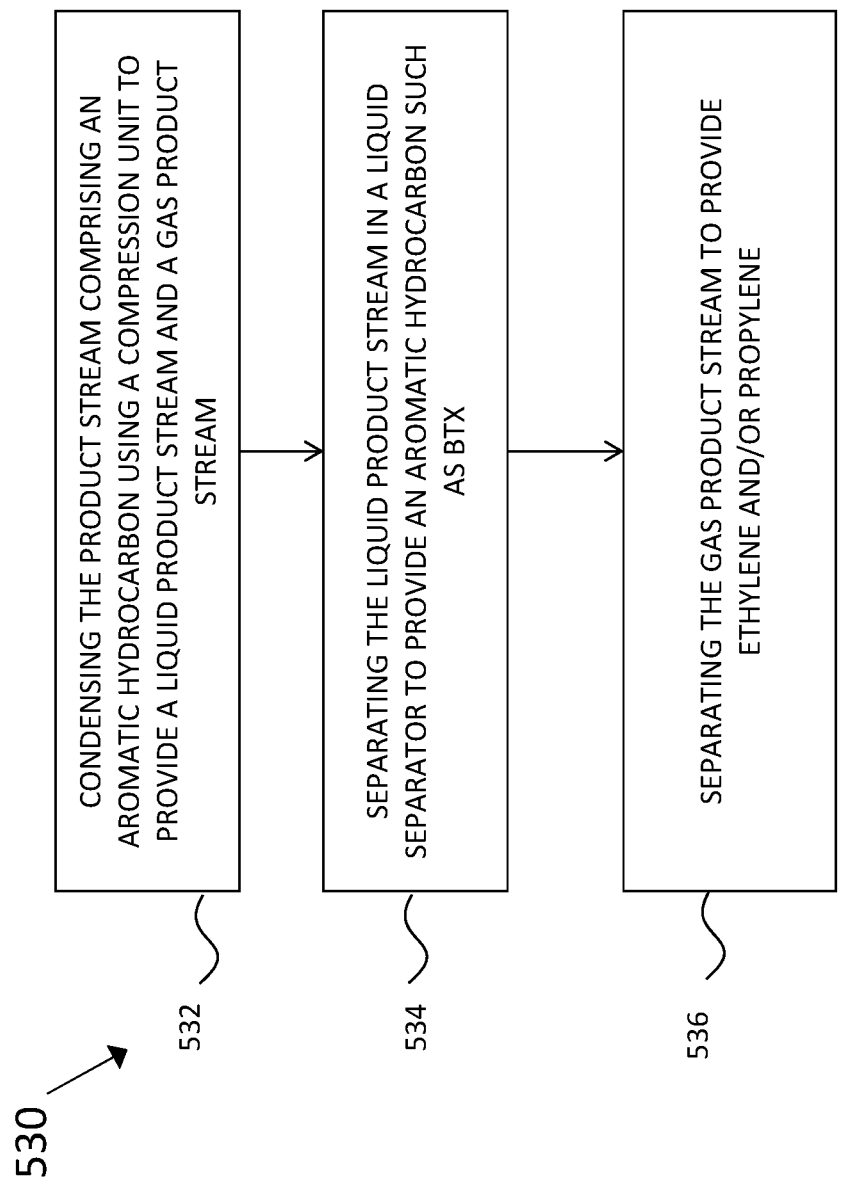

Referring to FIG. 6, a fourth exemplary system 300 is illustrated in accordance with some embodiments. FIG. 6 is a detailed illustration of another example of the exemplary system 200 as described in FIG. 3. The fourth exemplary system 300 includes a cracker unit 302 (e.g., an ethane cracker unit) and aromatics production unit or aromatization reactor 304.

Stream 301, an ethane feed stream, is fed to the cracker unit 302. In the cracker unit 302, ethane is converted into an olefinic product stream 303 primarily comprising ethylene. The olefinic product stream 303 may further optionally include ethane, ethylene, propane, propylene, butane, butadiene, and acetylene. The olefinic stream 303 is fed to the aromatization reactor 304 to be converted primarily into an aromatic stream 305 primary including BTX, with less amounts of ethane, methane, butadiene, propane, propylene, butane, acetylene, hexane, naphthalene and various other compounds.

This aromatic stream 305 is fed to a compressor unit 306 to provide a liquid product dropout stream 307, and a compressed gas stream 312.

The liquid product dropout stream 307 primarily includes BTX, C4-C6 compounds, and C8+ compounds. The liquid product dropout stream 307 is fed to an aromatics separation unit 308, which includes a plurality of distillation towers. Inside the aromatics separation unit 308, a fuel gas stream 309 consisting primarily of C4-05 compounds is separated from a BTX product stream 310. A further separation may be performed to separate a heavy liquid product stream 311, for example, comprising C8+ hydrocarbons.

The compressed gas stream 312, which primarily includes ethane, ethylene, methane, hydrogen, propane and propylene, is sent to a membrane separation unit 313. Inside the membrane separation unit 313, the permeate stream 315 primarily including methane and hydrogen is fed to a pressure swing adsorption (PSA) unit 316. Inside the PSA unit 316, a hydrogen product stream 317 is separated from a methane fuel gas stream 318. The effluent stream 314 primarily including ethane, ethylene, propane and propylene is recycled back to the ethane cracker unit 301 as a secondary feed stream for the ethane cracker unit 302.

Referring to FIGS. 7A-7C, an exemplary method 500 for making aromatic hydrocarbons from light alkanes and/or alkenes is illustrated.

Referring to FIG. 7A, at step 502, a light alkane is provided into a cracker unit as described above. In some embodiments, the light alkane comprises or is alkane.

At step 504, the light alkane is converted into an olefin-containing hydrocarbon comprising at least one alkene inside the cracker unit. The first stream of the olefin-containing hydrocarbon includes a portion or all of the olefin-containing hydrocarbon inside the cracker unit. In some embodiments, the light alkane comprises or is ethane, and the at least one alkene comprises 40 wt. % such as at least 50 wt. % of ethylene, and optionally propylene.

At step 506, a first stream of the olefin-containing hydrocarbon (e.g., stream 203, 213, or 203 as described above) is fed from the cracker unit into an aromatization reactor in an aromatization unit fluidly coupled with the cracker unit. In some embodiments, the light alkane comprises an alkane selected from the group consisting of methane, ethane, propane, butane, and a combination thereof. The first stream of the olefin-containing hydrocarbon stream comprises at least 50 wt. % of the at least one alkene (e.g., ethane).

At step 508, the olefin-containing hydrocarbon inside an aromatization reactor in an aromatization unit is converted into a product stream. The product stream comprises an aromatic hydrocarbon selected from the group consisting of benzene, toluene, xylenes, and a combination thereof.

At step 510, separation of the product stream is performed to obtain a first product (e.g., stream 241 or 310 as described above) comprising benzene, toluene, xylenes, or a combination thereof, and optionally a second product comprising C8+ hydrocarbons. In some embodiments, wherein the first product comprises benzene, toluene, and xylenes (BTX).

In some embodiments, the first stream of the olefin-containing hydrocarbon is converted into the aromatic hydrocarbon with a selectivity of higher than 40%, in a range of from 40-100%, for example, in a range of from 40% to 90%, from 50% to 90%, and from 50% to 80%.

In the aromatization reactor, a catalyst is used to obtain the conversion and selectivity. Such aromatization catalyst is used in the conversion of lower olefin into aromatic hydrocarbons. The aromatization catalyst and a preparation method thereof are described in Chinese Application No. 201910654576.2, filed Jul. 19, 2019, which is incorporated herein by reference.

In some embodiments, the aromatization catalyst comprises a microporous material and an adhesive, and optionally a metal active component. The adhesive is a compound containing elements aluminum and elements phosphorus, and the molar ratio of the elements aluminum to the elements phosphorus is more than or equal to 1 and less than 5. The ratio of the acidity of the strongly acidic sites to the acidity of the weakly acidic sites of the aromatization catalyst is less than 1. The microporous material may be a molecular sieve, such as ZSM-5. In some embodiments, ZSM-5 having a silica-alumina ratio of not more than 50 is used.

In some embodiments, the adhesive is aluminum phosphate and optionally alumina. The metal active component is one or more of Pt, Ni, Co, Cu, Zn, Fe, Pd, Rh, Ru, Re, Mo, W, Au and Ga, or any combination thereof.

In some embodiments, the weight ratio of the microporous material to the adhesive is 1:0.05-1, wherein the adhesive is calculated by elements aluminum in the adhesive. The content of the metal active component is 0% by weight to 1% by weight based on the total amount of the aromatization catalyst.

The catalyst can be made using different methods. For example, a first method includes mixing, extruding and calcinating the microporous material, the alumina and the phosphorus-containing solution to obtain a catalyst. The molar ratio of elements aluminum in the alumina to elements phosphorus in the phosphorus-containing solution is more than 1 and less than 5. Optionally, the catalyst can be subject to a hydrothermal treatment; and/or, optionally, a metal active component is supported on the catalyst surface.

For another example, a second method includes the following steps: mixing and extruding the microporous material and alumina, and optionally carrying out hydrothermal treatment to obtain an extrudate; and mixing, extruding and calcinating the extrudate and a phosphorus-containing solution to obtain a catalyst. The molar ratio of elements aluminum in alumina to elements phosphorus in the phosphorus-containing solution is more than 1 and less than 5. Optionally, a metal active component is supported on the catalyst surface.

The aromatization catalyst can perform aromatization reaction on lower olefin to generate aromatic hydrocarbons, has high stability and good selectivity for aromatic hydrocarbons products, and can also effectively reduce the generation of methane and coke.

Referring to FIG. 7B, in some embodiments, the method 500 further comprises one or more of the steps in the sub-method 520.

At step 522, a second stream of the olefin-containing hydrocarbon (e.g., stream 212) is fed into a cracker separator (e.g., separator 220) in the cracker unit.

At step 524, the second stream of the olefin-containing hydrocarbon is separated inside the cracker separator to provide an ethylene stream and a propylene stream.

At step 526, a hydrocarbon-containing residue gas (e.g., gas stream 245) is separated from the product stream in the aromatization separator (e.g., separator 240), and then is directed into the cracker separator.

At step 528, an alkane-containing gas (e.g., gas stream 228) is separated in the cracker separator (e.g., separator 220), and recycled back to the cracker reactor.

In some embodiments, an integrated system 300 of FIG. 6 is used. Such an integrated system includes a cracker unit, an aromatization unit, and a compress unit connected in series. The method 500 further comprises additional steps in sub-method 530 as shown in FIG. 7C.

Referring to FIG. 7C, at step 532, the product stream comprising an aromatic hydrocarbon is condensed using a compression unit 306 fluidly coupled with the aromatization unit to provide a liquid product stream 307 and a gas product stream 312.

At step 534, the liquid product stream is separated in a liquid separator 308 fluidly coupled with the condenser to provide an aromatic hydrocarbon selected from the group consisting of benzene, toluene, xylenes, and a combination thereof.

At step 536, the gas product stream is separated to provide products such as ethylene and/or propylene as described above.

In the method provided in the present disclosure, the steps are performed continuously and/or concurrently in an integrated system. Sometimes, the method can be performed in a batch process.

Other olefin production pathways may be used to pair with the aromatization reactor or ethylene could be sourced from a supplier. A single step reactor can be also used to convert from ethane to aromatics.

EXPERIMENTAL

Table 1 shows Examples 1-5 ("Ex. 1" to "Ex. 5") and the results. All the streams were measured in a unit of tons/hour. Ethane was used as the raw material feedstock. In Examples 1-4, the feed rate of raw material ethane was kept constant at 119.1 tons per hour. In Example 5, the feed rate was increased until the ethylene product rate (stream 221 in FIG. 4) was the same as in Example 1.

Example 1 is the base case performed in the system of FIG. 4, where 0% of the effluent of ethane cracker reactor, i.e., no stream 213, is sent to an aromatization unit. No aromatization reactor or aromatization separations unit was used. Such a system is equivalent to in the system of FIG. 2.

In Example 2, in the system of FIG. 4, 20% of the effluent of the ethane cracker reactor 210, i.e., stream 213, was sent to the aromatization reactor 230. The remaining 80% of effluent from the ethane cracker reactor 210, i.e., stream 212, was sent to the ethane cracker separation unit 220.

In Example 3, in the system of FIG. 4, 50% of the effluent of the ethane cracker reactor 210, i.e., stream 213, was sent to the aromatization reactor 230. The remaining 50% of effluent from the ethane cracker reactor 210, i.e., stream 212, was sent to the ethane cracker separation unit 220.

In Example 4, in the system of FIG. 5 (or FIG. 5), 100% of the effluent of the ethane cracker reactor 210, i.e., stream 213, was sent to the aromatization reactor 230. No stream 212 was sent to the ethane cracker separation unit 220.

Example 5 is similar to Example 2, except that the ethane feed rate was increased until the ethylene product rate (stream 221 in FIG. 4) was the same as in Example 1.

The conversion rate in each experimental is close to 100%. Based on the total feed to the aromatization reactor and the BTX product by weight, the selectivity of the BTX conversion is 52.%, 53.7%, 54.8% and 52.7%, for Examples 2, 3, 4, and 5, respectively.

TABLE 1

| Component | Ex. 1 | Ex. 2 | Ex. 3 | Ex. 4 | Ex. 5 |
|---|---|---|---|---|---|
| % effluent from ethane cracker reactor to aromatization reactor | 0% | 20% | 50% | 100% | 20% |
| Ethane Fed (Stream 201) | 119.1 | 119.1 | 119.1 | 119.1 | 149.1 |
| Ethylene Product (Stream 221) | 94.8 | 75.7 | 50.1 | 7.6 | 94.8 |
| Propylene Product (Stream 222) | 2.9 | 2.3 | 1.6 | — | 2.9 |
| Hydrogen Product (Stream 225) | 6.7 | 7.2 | 8.1 | 9.5 | 9.1 |
| Methane Product (Stream 224) | 10.2 | 12.9 | 17.2 | 24.6 | 16.2 |
| C4+ Product (Streams 223 + 247) | 4.5 | 7.9 | 8.9 | 9.6 | 9.8 |
| BTX Product (Stream 241) | — | 12.6 | 32.0 | 65.3 | 15.7 |
| Heavies Product (Stream 242) | — | 0.5 | 1.2 | 2.5 | 0.6 |

* Except the percentages, the units for all other values are Tons/hour.

Although the subject matter has been described in terms of exemplary embodiments, it is not limited thereto. Rather, the appended claims should be construed broadly, to include other variants and embodiments, which may be made by those skilled in the art.

What is claimed is:

1. A system for producing aromatics, comprising:
a cracker unit configured to convert a light alkane into an olefin-containing hydrocarbon comprising at least one alkene, wherein the light alkane is ethane and wherein the at least one alkene is ethylene; and
an aromatization unit;
wherein the cracker unit is configured to at least partially feed the olefin-containing hydrocarbon directly into the aromatization unit, wherein the olefin-containing hydrocarbon comprises at least 40 wt. % of the at least one alkene, and wherein the aromatization unit is configured to convert the olefin-containing hydrocarbon therein into a product stream comprising an aromatic hydrocarbon selected from the group consisting of benzene, toluene, xylenes, and a combination thereof.

2. The system of claim 1, wherein the cracker unit includes a steam cracker.

3. The system of claim 1, wherein the olefin-containing hydrocarbon further comprises propylene.

4. The system of claim 1, wherein the cracker unit comprises a cracker reactor and optionally a cracker separator; and the aromatization unit comprises an aromatization reactor and an aromatization separator.

5. The system of claim 4, wherein the cracker reactor is configured to feed a first stream of the olefin-containing hydrocarbon into the aromatization reactor, and feed a second stream of the olefin-containing hydrocarbon into the cracker separator.

6. The system of claim 5, wherein the cracker separator is configured to separate the second stream of the olefin-containing hydrocarbon to provide an ethylene stream and a propylene stream.

7. The system of claim 4, wherein the aromatization reactor is configured to direct the product stream comprising an aromatic hydrocarbon into the aromatization separator, and the aromatization separator is configured to separate the product stream to provide a first product comprising benzene, toluene, xylenes, or a combination thereof.

8. The system of claim 7, wherein the aromatization separator is configured to further provide a second product comprising C8+ hydrocarbon.

9. The system of claim 1, further comprising a compress unit configured to condense the product stream comprising an aromatic hydrocarbon from the aromatization unit to provide a liquid product stream and a gas product stream.

10. The system of claim 9, further comprising a liquid separator configured to separate the liquid product stream to provide an aromatic hydrocarbon selected from the group consisting of benzene, toluene, xylenes, and a combination thereof.

11. A method for producing aromatics, comprising:
providing a light alkane into a cracker unit, wherein the light alkane is ethane;
converting the light alkane into an olefin-containing hydrocarbon comprising at least one alkene inside the cracker unit;
directly feeding a first stream of the olefin-containing hydrocarbon from the cracker unit into an aromatization reactor in an aromatization unit fluidly coupled with the cracker unit, the first stream of the olefin-containing hydrocarbon stream comprises at least 40 wt. % of the at least one alkene the at least one alkene is ethylene; and
converting the olefin-containing hydrocarbon inside an aromatization reactor in an aromatization unit into a product stream comprising an aromatic hydrocarbon selected from the group consisting of benzene, toluene, xylenes, and a combination thereof.

12. The method of claim 11, wherein the stream of the olefin-containing hydrocarbon includes a portion or all of the olefin-containing hydrocarbon inside the cracker unit.

13. The method of claim 11, wherein the olefin-containing hydrocarbon stream further comprises propylene.

14. The method of claim 11, wherein the first stream of the olefin-containing hydrocarbon is converted into the aromatic hydrocarbon with a selectivity of higher than 40%.

15. The method of claim 11, further comprising separating the product stream to a first product comprising benzene, toluene, xylenes, or a combination thereof, and optionally a second product comprising C8+ hydrocarbons.

16. The method of claim 15, wherein the first product comprises benzene, toluene, and xylenes.

17. The method of claim 11, further comprising:
feeding a second stream of the olefin-containing hydrocarbon into a cracker separator in the cracker unit; and
separating the second stream of the olefin-containing hydrocarbon inside the cracker separator to provide an ethylene stream and a propylene stream.

18. The method of claim 17, further comprising:
separating an hydrocarbon-containing residue gas from the product stream;
directing the alkane-containing residue gas into the cracker separator;
separating an alkane-containing gas in the cracker separator; and
recycling the alkane-containing gas back to the cracker reactor.

19. The method of claim 1, further comprising:
condensing the product stream comprising an aromatic hydrocarbon using a compression unit fluidly coupled with the aromatization unit to provide a liquid product stream and a gas product stream; and
separating the liquid product stream in a liquid separator fluidly coupled with the condenser to provide an aromatic hydrocarbon selected from the group consisting of benzene, toluene, xylenes, and a combination thereof.

20. The method of claim 1, wherein steps in the method are performed continuously in an integrated system.

21. The system of claim 4, wherein the aromatization separator is configured to separate a hydrocarbon-containing residue gas from the product stream and direct the alkane-containing residue gas into the cracker separator; and the cracker separator is configured to separate an alkane-containing gas therein and recycle the alkane-containing gas back to the cracker reactor.

* * * * *